(12) United States Patent
Petersen et al.

(10) Patent No.: US 9,693,855 B2
(45) Date of Patent: Jul. 4, 2017

(54) STENT GRAFT

(75) Inventors: Jesper Schade Petersen, Holmegaard (DK); Marianne Soerensen, Ringsted (DK); Tina Moerk, Ringsted (DK)

(73) Assignee: Cook Medical Technologies LLC, Bloomington, IN (US)

( * ) Notice: Subject to any disclaimer, the term of this patent is extended or adjusted under 35 U.S.C. 154(b) by 609 days.

(21) Appl. No.: 12/774,334

(22) Filed: May 5, 2010

(65) Prior Publication Data

US 2010/0286757 A1 Nov. 11, 2010

(30) Foreign Application Priority Data

May 6, 2009 (GB) .................... 0907809.8

(51) Int. Cl.
*A61F 2/07* (2013.01)
*A61F 2/95* (2013.01)
*A61F 2/966* (2013.01)
*A61F 2/89* (2013.01)

(52) U.S. Cl.
CPC ............... *A61F 2/07* (2013.01); *A61F 2/966* (2013.01); *A61F 2/89* (2013.01); *A61F 2002/075* (2013.01); *A61F 2230/005* (2013.01); *A61F 2230/0013* (2013.01); *A61F 2230/0054* (2013.01)

(58) Field of Classification Search
CPC ........ A61F 2002/075; A61F 2230/0054; A61F 2/07; A61F 2/89; A61F 2002/067; A61F 2250/0048; A61F 2/06
USPC ................................. 623/1.11–1.54
See application file for complete search history.

(56) References Cited

U.S. PATENT DOCUMENTS

| | | | |
|---|---|---|---|
| 5,713,917 A * | 2/1998 | Leonhardt et al. | 606/194 |
| 5,824,037 A | 10/1998 | Fogarty et al. | |
| 6,071,307 A | 6/2000 | Rhee et al. | |
| 6,344,052 B1 * | 2/2002 | Greenan et al. | 623/1.1 |
| 6,451,053 B1 | 9/2002 | Dehdashtian et al. | |
| 7,294,147 B2 | 11/2007 | Hartley | |
| 2005/0049674 A1 | 3/2005 | Berra et al. | |
| 2005/0273154 A1 * | 12/2005 | Colone | A61F 2/07 623/1.13 |
| 2006/0195172 A1 | 8/2006 | Luo et al. | |
| 2006/0195177 A1 | 8/2006 | Kaufmann et al. | |
| 2007/0203566 A1 * | 8/2007 | Arbefeuille et al. | 623/1.13 |
| 2008/0114441 A1 | 5/2008 | Rust et al. | |
| 2008/0294234 A1 * | 11/2008 | Hartley | A61F 2/07 623/1.12 |

FOREIGN PATENT DOCUMENTS

| | | |
|---|---|---|
| EP | 1772120 A2 | 4/2007 |
| EP | PCT/US2010/033745 | 7/2010 |
| EP | PCT/US2010/033754 | 7/2010 |
| WO | 0121102 A1 | 3/2001 |

* cited by examiner

*Primary Examiner* — Ann Schillinger
(74) *Attorney, Agent, or Firm* — Brinks Gilson & Lione

(57) ABSTRACT

A stent graft 30 has a bare end stent 31 which partially overlaps the next stent 32 with the end 36 of the graft material 34 being shaped to follow the distal peaks 35 of the end stent and the proximal peaks 47 of the next stent. The proximal peaks 37 of the end stent have a greater radius of curvature than the distal peaks 35 of the end stent.

17 Claims, 2 Drawing Sheets

STENT GRAFT

TECHNICAL FIELD

The present invention relates to a stent graft and in particular to a stent graft for deployment in a curved body vessel such as the aortic arch.

BACKGROUND OF THE INVENTION

A problem with the deployment of stent grafts in the aortic arch is that a satisfactory engagement against the interior of the body vessel wall has to be maintained at the same time as matching the curved shape of the aortic arch. Satisfying both constraints involves a compromise in design and conventional stent grafts do not bend satisfactorily around the aortic arch.

Another design constraint is that the proximal end stent should be at least partly bare, i.e. have no graft material thereon, in order that blood flow may be maintained with side vessels.

US 2005/0049674 A1 discloses a stent graft having a proximal end stent which is substantially bare. The distal end of the proximal stent partially overlaps with the proximal end of the second stent. Viewed from the side, the end of the graft material is a straight line connecting the proximal bends of the second stent.

US 2006/0195172 A1 also discloses a stent graft with a substantially bare end stent which partially overlaps the second stent.

Stent grafts are also disclosed in U.S. Pat. Nos. 5,824,037 and 7,294,147 for example.

US 2006/0195177 discloses a stent graft in which stent graft material between two end rings is shaped with a V-recess to allow access to side vessels of the aortic arch.

A recent proposal for stent grafts for curved vessels is the so-called tri-fold device. This offers some improvement over conventional devices, but in certain cases the two most proximal stents can touch each other during deployment, which may cause the curvature of the stent graft to differ from the curvature of the body vessel;

SUMMARY OF THE INVENTION

Aspects of the present invention seek to provide a stent graft, at least the proximal end of which can curve to match the curvature of a body vessel.

Other aspects of the invention seek to provide a stent graft, at least the proximal end of which can be compressed for passage through a relatively narrow pathway through the body before it is expanded at its deployment site.

According to a first aspect of the present invention, there is provided a stent graft member comprising a plurality of stents secured to graft material in which the distal end of a proximal, at least partially bare, stent overlaps longitudinally with the proximal end of the next stent, with distal peaks of the proximal stent lying between proximal peaks of the next stent, wherein the proximal end of the graft material has a shape with proximal peaks and distal peaks.

An advantage of this configuration is that is satisfies several design constraints. For example, it provides a flexible interconnection between the end stent and the next stent to enable the stent graft to more closely follow the inner curve of the aortic arch, and thus a more precisely aligned location of the stent graft in the body vessel. Furthermore, the configuration permits the stent graft, and in particular its proximal end, to be folded into a compact arrangement when compressed. This can be attributed, at least in part, to the absence of graft material where it is not required.

Preferably, the stents are formed of wire and the distal peaks of the bare stent overlap the proximal peaks of the next stent, at least in a compressed configuration of the stent graft member, by a distance equal to at least twice the thickness of the wire. This further assists in enabling a compact compressed configuration. Viewed circumferentially, there is effectively double thickness of wire at each stent peak; by avoiding alignment of the distal peaks of the proximal stent and the proximal peaks of the next stent, resistance to compression is avoided.

In an alternative arrangement, when folded in a compressed configuration, the distal end of the proximal stent does not overlap longitudinally with the proximal end of the next stent.

In preferred arrangements the distal peaks of the curve in the graft material are located at or adjacent distal peaks of the proximal stent, and proximal peaks of the curve are located at or adjacent proximal peaks of the next stent. This provides a substantially symmetrical configuration which can be neatly folded into a compressed configuration.

Preferably, the proximal peaks of the proximal stent have a greater radius of curvature than the distal peaks of the proximal stent. The relatively large radius of the proximal peaks avoids their undesired entry into side vessels of the aorta. The relatively small radius of curvature of the distal peaks contributes to a smaller volume of wire which assists in packing when the end of the stent is compressed.

According to a second aspect of the present invention, there is provided a method of folding a stent graft member according to claim 1 comprising exerting radially inward forces on the proximal end of the stent graft member whereby the distal peaks of the end stent are moved radially inwardly beyond the proximal peaks of the next stent into a compressed configuration in which the distal peaks of the end stent are not aligned longitudinal with the proximal peaks of the next stent.

In one preferred method, in the compressed configuration, there is a longitudinal overlap between the distal peaks of the end stent and the proximal peaks of the next stent. Where the stents are made of wire, the longitudinal overlap of the peaks is equal to at least twice the thickness of the wire. Thus although there is still an overlap of the stents, the distal peaks of the end stent are sufficiently out of longitudinal alignment with the proximal peaks of the next stent that a concentration of wire material in one place is avoided.

In an alternative method, in the compressed configuration, there is no longitudinal overlap between the distal peaks of the end stent and the proximal peaks of the next stent.

BRIEF DESCRIPTION OF THE DRAWING

Preferred embodiments of the present invention will now be described, by way of example only, with reference to the accompanying drawings, of which.

DETAILED DESCRIPTION

Figure 1:
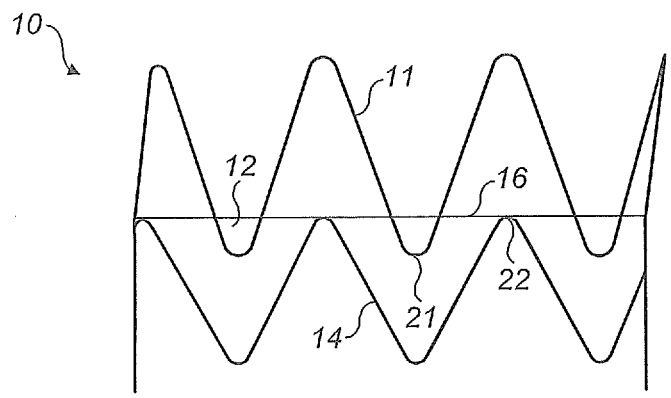
FIG. 1 shows a side view of the proximal end of a stent graft member in accordance with the prior art.

Referring to the drawings, FIG. 1 shows a stent graft 10 in accordance with the prior art. A proximal end stent 11 is substantially bare, that is only a relatively small part of the stent is covered with graft material 12. For most of its length, the wire forming stent 11 has no graft material on either side; at intervals, relatively short lengths of the wire have graft material on all sides. The next stent 14 is completely covered by the graft material. Viewed in the sideways or radial direction of the Figure, the end 16 of the graft material is a straight line. The graft material 12 and the stent members 11, 14 attached thereto are substantially circular in cross-section.

As seen in FIG. 1, the distal peaks 21 of stent 11 overlap the proximal peaks 22 of the next stent 12 in the longitudinal direction. The peaks 21 and 22 alternate in regular manner around the periphery of the stent graft.

Problems can arise when compressing the stent graft 10 for passage through a relatively narrow body vessel to a deployment site. In particular, the graft material can interfere with the desired inward movement of the stents, for example it can directly constrain relative movement of the stents, or the material may fold to block the desired movement.

FIGS. 2 to 6 show the proximal end of an embodiment of a stent graft 30 in accordance with the present invention. The stent graft 30 is typically deployed in the aortic arch with a second stent graft (not shown) attached to its distal end. The length of the stent graft 30 lies between 145 and 220 mm and the length of the distal stent graft lies between 145 and 195 mm with a three stent overlap of the two stent grafts. The diameter of stent graft 30 lies within the range 22 mm to 46 mm and preferably in the range 30 mm to 40 mm. The stent graft 30 has a substantially free or bare stent 31 which differs from the stent 11 of FIG. 1 in a number of ways. Firstly, the stent 31 is attached by suture stitches 33 at or directly adjacent to respective distal peaks 35 of the stent. Thus there is, at most, only a very small area of graft material 34 covering stent 31. Secondly, the proximal peaks 37 of stent 31 have a relatively large radius of curvature compared to the distal peaks 35.

Stent 32 is conveniently configured to have five proximal peaks 37.

As before, the next stent 32 is completely covered by graft material 34 and is arranged with its proximal peaks 47 arranged regularly between the distal peaks 35 of stent 31. Stent 32 is conveniently configured as a laser cut canula stent which is formed from a tube in the manner of a silver stent with internal barbs.

Instead of being straight, the edge 36 of the graft material has a sinusoidal shape with its proximal peaks coinciding with the proximal peaks 47 of stent 32 and with its distal peaks aligned with and almost coincident with the distal peaks 35 of stent 31. The peak-to-peak dimension or wave "w" of the edge 36 is within the range 1-3 mm, preferably 2 mm.

Table 1 below gives the preferred internal diameter in French of a deployment sheath for use in introducing stent grafts of various diameter into a body vessel. The Table also gives the preferred number of points on the stents of the grafts.

TABLE 1

| Graft Diameter in mm | Sheath I.D. (Fr) | Number of Points on Stent |
|---|---|---|
| 22 | 16 | 5 |
| 24 | 16 | 5 |
| 26 | 16 | 5 |
| 28 | 16 | 5 |
| 30 | 16 | 5 |
| 32 | 18 | 6 |
| 34 | 18 | 6 |
| 36 | 18 | 6 |
| 38 | 18 | 6 |
| 40 | 18 | 7 |
| 42 | 18 | 7 |
| 44 | 20 | 8 |
| 46 | 20 | 8 |

Figure 2:
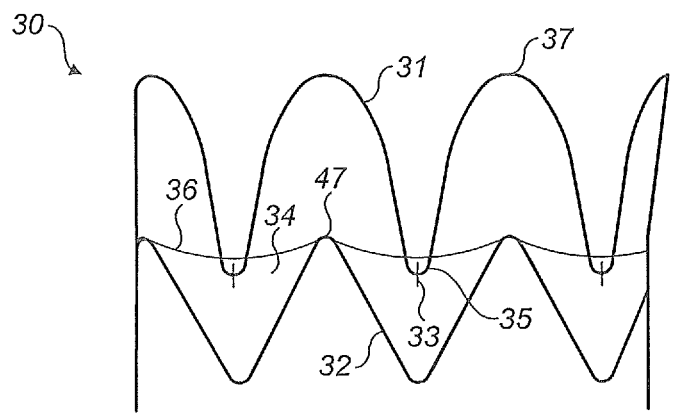
FIG. 2 shows the corresponding view of a stent graft member in accordance with the present invention in its expanded configuration.
Figure 3:
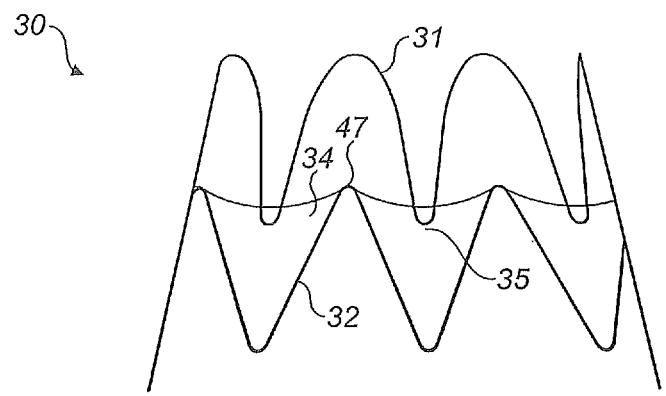
FIG. 3 shows a side view of the stent graft member of FIG. 2 in a partially-folded configuration.
Figure 4:
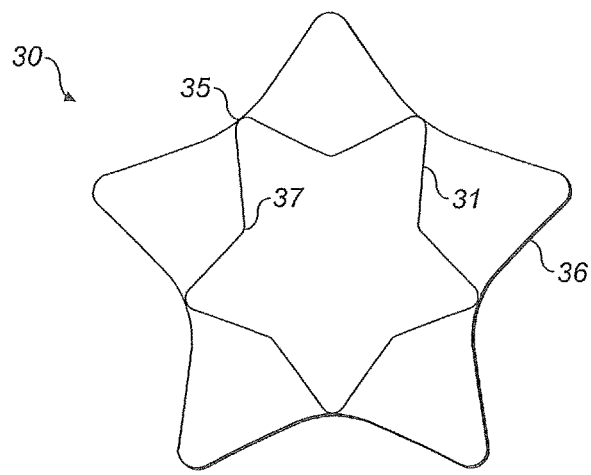
FIG. 4 shows an end view of the stent graft member in the partially-folded configuration of FIG. 3 but with the stents other than the end stent omitted for the purposes of clarity.

FIG. 2 shows the stent graft 30 in expanded configuration before folding or compression into a compact form before passage through a body vessel. FIGS. 3 and 4 show the stent graft 30 as folding commences. The distal peaks 35 of the end stent 31 move radially inwardly beyond the proximal peaks 47 of the next stent 32 to enable full compression. The peaks 35 are arranged at a sufficient axial spacing from the peaks 47 such that when folded the peaks 35 do not overlap the peaks 47.

Figure 5:
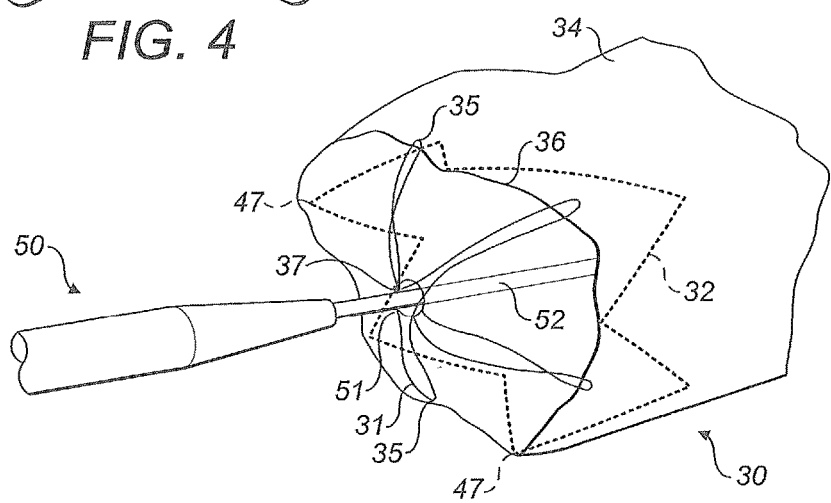
FIG. 5 shows the stent graft member of FIGS. 2 to 4 in conjunction with an introducer apparatus.

FIG. 5 shows the stent graft member 30 in its configuration after it has been deployed in a body vessel and expanded, but before it is released from an introducer apparatus 50. The proximal peaks 37 of the end stent 31 are held at the centre by the graft member by release wires 51 extending through apertures in a sleeve 52 of the introducer apparatus. For the purposes of clarity, the next stent 32 is indicated in broken lines in FIG. 5.

Figure 6:
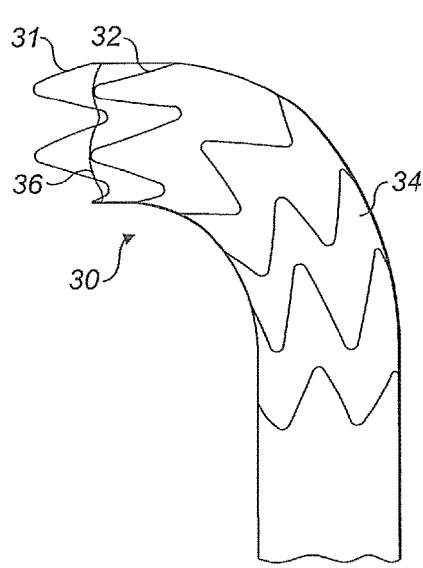
FIG. 6 shows a side view of the proximal end of the stent graft member of FIGS. 2 to 5 in its deployed configuration.

FIG. 6 shows the stent graft member 30 in its configuration after full deployment in a curved body vessel. The end stent 31 has been fully released for full expansion so that it can firmly engage the walls of the body vessel to hold the stent graft member in position.

The above-described stent graft has the advantage of being highly compressible. Volume is saved by the end stent being substantially completely bare. Moreover, the shaping of the end 36 of the graft material means that there is more space available for the stents; in addition by connecting the stents 31, 32, the graft material produces the desired relative movement of the stents so that, during compression, the distal peaks 35 move radially inwardly beyond the proximal peaks 47.

The packing efficiency of the arrangement is further improved by the relatively small radius of curvature of the distal peaks 35, which leads to a small volume. The relatively large radius of curvature of the proximal peaks 37 prevents these peaks from accidental entry into side blood vessels, while maintaining the desired engagement with the wall of the aortic arch.

During deployment of the stent graft 30, the flexible interconnection between the end stent 31 and the next stent 32 enables the end of the graft to more closely follow the inner curve of the aortic arch, which in turn leads to a more precisely aligned location of the graft in the body vessel. How this is achieved will now be briefly described. As a sheath covering the positioned stent graft is withdrawn, an introducer tip of the deployment assembly is arranged to automatically bend more tightly around the inner curve of the aortic arch. This bending causes the stent graft 30 to bend and the distal peaks 35 to fold inwardly and, by means of the graft material 34, pull in the proximal peaks 47 of the next stent 32 to allow precise and controlled bending of the graft 30.

Various modifications may be made to the above-described arrangement. The edge 36 of the graft material may be of any suitable curved or sinuous shape. The edge may have a regular saw-tooth shape with adjacent proximal and distal peaks being connected by straight lines.

The stent-graft may be deployed in any curved body vessel instead of the aortic arch.

What is claimed is:

1. A stent graft having an expanded configuration and a compressed configuration, the stent graft comprising a plurality of stents secured to graft material, the graft material having a proximal edge having a sinusoidal shape about the edge of the graft material;
the plurality of stents including a proximal stent and a distally adjacent stent each having a sinusoidal shape,
the proximal stent having uncovered proximal peaks extending beyond the proximal edge of the graft material and distal peaks extending below the proximal edge of the graft material,
the distally adjacent stent having proximal peaks that substantially abut the proximal edge of the graft material and distal peaks extending below the proximal edge of the graft material,
wherein the distal peaks of the proximal stent lie between the proximal peaks of the distally adjacent stent and below the proximal peaks of the distally adjacent stent, and
wherein the sinusoidal shape of the proximal edge of the graft material does not follow the sinusoidal shape of either the proximal stent or the distally adjacent stent, and
wherein in the compressed configuration, the distal peaks of the proximal stent extend radially inwardly beyond the proximal peaks of the distally adjacent stent;
wherein the sinusoidal shape of the edge of the graft material has valleys and peaks and the distal peaks of the proximal stent are located at or adjacent, the valleys of the edge of the graft material and the proximal peaks of the distally adjacent stent are located at or adjacent the peaks of the graft material.

2. The stent graft of claim 1, wherein the stents are formed of wire and the distal peaks of the proximal stent extend below the proximal peaks of the distally adjacent stent, at least in a compressed configuration of the stent graft, by a distance equal to at least twice the thickness of the wire.

3. The stent graft of claim 1, wherein the proximal peaks of the proximal stent have a greater radius of curvature than the distal peaks of the proximal stent.

4. The stent graft of claim 1, wherein the proximal peaks of the proximal stent have a greater radius of curvature than the distal peaks of the proximal stent.

5. The stent graft of claim 1, wherein the distance between the peaks of the proximal edge of the graft material is between 1 mm to 3 mm.

6. The stent graft of claim 1, wherein the proximal stent is formed of wire and, wherein all of the proximal stent but the distal peaks of the proximal stent are free of graft material on all sides.

7. The stent graft of claim 1, wherein the dimensions of the stents and the graft material are selected such that the stent graft is able to be folded to a configuration in which the distal peaks of the proximal stent do not overlap longitudinally with the proximal peaks of the distally adjacent stent.

8. A stent graft having an expanded configuration and a compressed configuration comprising a plurality of stents secured to graft material,
the graft material having a sinusoidally shaped proximal edge,
the plurality of stents comprising a proximal stent having proximal peaks and distal peaks, and a distally adjacent stent having proximal peaks and distal peaks,
wherein the proximal peaks of the proximal stent extend beyond the sinusoidally shaped proximal edge, the distal peaks of the proximal stent extend below the sinusoidally shaped proximal edge, the proximal peaks of the distally adjacent stent lie between the distal peaks of the proximal stent and extend substantially to the edge of the graft material,
wherein each stent has a sinusoidal shape wherein the sinusoidal shape of each stent does not follow the edge of the graft material, and wherein in the compressed configuration, the distal peaks of the proximal stent extend radially inwardly beyond the proximal peaks of the distally adjacent stent, and
wherein the distal peaks of the sinusoidally shaped proximal edge of the graft material are located at or adjacent distal peaks of the proximal stent and proximal peaks of the graft material are located at or adjacent proximal peaks of the distally adjacent stent.

9. The stent graft according to claim 8, wherein the graft material of the proximal peaks coincides with the proximal peaks of the distally adjacent stent.

10. The stent graft member according to claim 9, wherein the stents are formed of wire and the distal peaks of the proximal stent overlap the proximal peaks of the distally adjacent stent, at least in a compressed configuration of the stent graft member, by a distance equal to at least twice the thickness of the wire.

11. The stent graft member according to claim 9, wherein the proximal peaks of the proximal stent have a greater radius of curvature than the distal peaks of the proximal stent.

12. The stent graft member according to claim 8, wherein the proximal peaks of the proximal stent have a greater radius of curvature than the distal peaks of the proximal stent.

13. A stent graft having an expanded configuration and a compressed configuration, the stent graft comprising:
a generally tubular graft having a proximal end, a distal end, and a proximal edge at the proximal end, the proximal edge having an undulating pattern about the edge, the undulating pattern having valleys and peaks,
a first stent having proximal apices and distal apices, the proximal apices extending entirely beyond the proximal edge of the graft material and not connected to the graft material, and the distal apices extending below the proximal edge and attached to the graft material,
a second stent immediately adjacent and substantially distal to the first stent, the second stent having proximal apices and distal apices,
wherein the distal apices of the first stent lie between the proximal apices of the second stent and longitudinally below the proximal apices of the second stent,
wherein each of the distal apices of the first and second stents extend below the valleys of the edge of the graft, and the proximal apices of the second stent are attached to the graft at the peaks of the edge of the graft,
wherein each of the first stent and the second stent have a shape wherein the shapes of first and second stents do not follow the proximal edge of the graft, wherein in the compressed configuration, the distal apices of the first stent extend radially inwardly away from proximal apices the second stent such that the distal apices of the first stent and the proximal apices of the second stent do not overlap.

14. A method of folding the stent graft of claim 13 comprising exerting radially inward forces on the proximal end of the stent graft member whereby the distal peaks of the end stent are moved radially inwardly beyond the proximal peaks of the next stent into a compressed configuration in which the distal peaks of the end stent are not aligned longitudinally with the proximal peaks of the next stent.

15. A method according to claim 14, wherein in the compressed configuration, there is a longitudinal overlap between the distal peaks of the end stent and the proximal peaks of the next stent.

16. A method according to claim 15 wherein the stents are formed of wire and the longitudinal overlap is equal to at least method according twice the thickness of the wire.

17. A method according to claim 14 wherein, in the compressed configuration, there is no longitudinal overlap between the distal peaks of the end stent and the proximal peaks of the next stent.

* * * * *